United States Patent [19]

Barile

[11] 4,387,259

[45] Jun. 7, 1983

[54] SELECTIVE ALKYLATION OF AROMATIC HYDROCARBONS USING A MIXED ETHYLENE/PROPYLENE ALKYLATION AGENT

[75] Inventor: George C. Barile, South Somerville, N.J.

[73] Assignee: Mobil Oil Corporation, New York, N.Y.

[21] Appl. No.: 283,863

[22] Filed: Jul. 16, 1981

[51] Int. Cl.³ .............................................. C07C 3/52
[52] U.S. Cl. .................................. 585/467; 585/468; 585/809; 585/830; 585/868
[58] Field of Search ............................... 585/467, 468

[56] References Cited

U.S. PATENT DOCUMENTS

| 3,086,998 | 4/1963 | Hervert | 585/467 |
| 3,755,483 | 8/1973 | Burress | 585/467 |
| 4,049,737 | 9/1977 | Dwyer et al. | 585/447 |
| 4,291,185 | 9/1981 | Kaeding | 585/467 |

FOREIGN PATENT DOCUMENTS

| 12504 | 6/1980 | European Pat. Off. | |
| 12514 | 8/1980 | European Pat. Off. | 585/467 |

OTHER PUBLICATIONS

Chem. Abstracts, vol. 55, No. 17548b.
Chem. Abstracts, vol. 76, No. 13942c.
Chem. Abst., vol. 55, No. 17548b.
Chem. Abst., vol. 76, No. 13942c.

*Primary Examiner*—Delbert E. Gantz
*Assistant Examiner*—A. Pal
*Attorney, Agent, or Firm*—C. A. Huggett; M. G. Gilman; G. W. Allen

[57] ABSTRACT

Aromatic hydrocarbons are selectively alkylated using an alkylating mixture containing both ethylene and propylene. By employing a zeolite ZSM-12 based alkylation catalyst, essentially only the propylene from the olefin-containing alkylation mixture will react with the aromatic hydrocarbon to thereby form both an alkylaromatic product enriched in propylated alkylaromatic and a propylene-free residual olefin-containing mixture enriched in the unreacted ethylene.

6 Claims, No Drawings

SELECTIVE ALKYLATION OF AROMATIC HYDROCARBONS USING A MIXED ETHYLENE/PROPYLENE ALKYLATION AGENT

BACKGROUND OF THE INVENTION

1. Field of the Invention

The present invention relates to selective catalytic alkylation, e.g., propylation, of aromatic hydrocarbons, e.g., benzene, using olefin mixtures containing both ethylene and propylene.

2. Description of the Prior Art

Alkylation of aromatic hydrocarbons with olefinic alkylation agents in the presence of zeolite catalysts such as ZSM-12 is known in the art. U.S. Pat. No. 3,755,483, issued Aug. 28, 1973 to G. T. Burress, for example, discloses that aromatic hydrocarbons such as benzene and toluene can be usefully alkylated either with ethylene or with propylene, in the vapor phase in the presence of ZSM-12 zeolite catalyst.

In commercial practice, however, alkylating agents comprising only one alkylating olefin such as pure ethylene or pure propylene are relatively expensive to obtain. Sources of olefin alkylating agents, for example, include refinery off-gases or tail gases which are streams containing dilute concentrations of mixtures of both ethylene and propylene and possibly higher olefins. A more common source of mixed ethylene/propylene feedstocks is the effluent produced by the thermal cracking of hydrocarbon streams in olefin production operations. Such a cracking product is generally much higher in mixed olefin content than are refinery off-gases. When such mixed olefin-containing gas streams from whatever source are used to alkylate aromatic compounds, a mixture of several types of alkylated aromatic products is frequently produced. For example, Zavgorodnii et al; Izvest. Vysshikh Ucheb. Zavedenii, Khim. i Khim. Tekhnol., Vol. 4, No. 1, pp. 128–132 (1961), and Lebedev et al; Khim. Prom. (Moscow), Vol 47, No. 10, pp. 744–746 (1971), both report the alkylation of benzene with gas streams containing ethylene and propylene over $AlCl_3$ and $BF_3.H_3PO_4$ catalysts to provide a product comprising both ethylbenzene and isopropylbenzene.

Attempts have been made to selectively provide a single alkylated aromatic product in processes utilizing mixed ethylene/propylene streams as the alkylating agent. U.S. Pat. No. 3,086,998; Issued Apr. 23, 1963 to G. L. Hervert, for example, discloses a process whereby propylated aromatic hydrocarbons can be selectively formed by using a boron trifluoride/modified sulfur-containing alumina catalyst to promote aromatic alkylation with an olefin mixture containing both ethylene and propylene. Notwithstanding such efforts, there is a continuing need to identify additional catalysts and catalyst systems which can be usefully employed to provide processes for the selective production of propylated aromatic compounds such as cumene using readily available, low cost ethylene/propylene streams as the alkylation agent.

SUMMARY OF THE INVENTION

The invention described and claimed herein provides such a process for selectively alkylating aromatic hydrocarbons with an olefin-containing alkylation mixture comprising from about 5 mol % to 95 mol % ethylene and from about 5 mol % to 95 mol % propylene. When aromatic hydrocarbon is contacted with such a mixture under alkylation conditions and in the presence of a zeolite ZSM-12 alkylation catalyst, both an alkylaromatic product enriched in propylated aromatic hydrocarbons and a residual propylene-free olefin-containing material enriched in unreacted ethylene are produced.

DETAILED DESCRIPTION OF THE INVENTION

Aromatic hydrocarbons are selectively alkylated in accordance with the process of the present invention. Many aromatic hydrocarbons can be used in such a process. Preferred aromatic hydrocarbons are monocyclic aromatic hydrocarbons, i.e., benzene hydrocarbons. Suitable aromatic hydrocarbons include benzene, toluene, ortho-xylene, meta-xylene, para-xylene, ethylbenzene, ortho-ethyltoluene, meta-ethyltoluene, para-ethyltoluene, 1,2,3-trimethylbenzene, 1,2,4-trimethylbenzene, 1,3,5-trimethylbenzene or mesitylene, normal propylbenzene, isopropylbenzene, etc. Higher molecular weight alkylaromatic hydrocarbons are also suitable and include aromatic hydrocarbons such as are produced by the alkylation or aromatic hydrocarbons with olefin polymers. Such products are frequently referred to in the art as alkylate, and include hexylbenzene, nonylbenzene, dodecyltoluene, pentadecyltoluene, etc. Very often alkylate is obtained as a high boiling fraction in which the alkyl group attached to the aromatic nucleus varies in size from about $C_9$ to about $C_{18}$. Other suitable alkylatable aromatic hydrocarbons include those with two or more aryl groups such as diphenyl, diphenylmethane, triphenyl, triphenylmethane, fluorene, stilbene, etc. Examples of other alkylatable aromatic hydrocarbons within the scope of this invention as starting materials containing condensed benzene rings include naphthalene, alpha-methylnaphthalene, beta-methylnaphthalene, anthracene, phenanthrene, naphthacene, rubrene, etc. Of the above aromatic hydrocarbons for use in the process of this invention, the benzene hydrocarbons are preferred, and of the preferred benzene hydrocarbons, benzene itself and toluene are particularly preferred.

The particular alkylating agent used in the present invention is an olefin mixture which essentially contains both ethylene and propylene. Ethylene generally comprises from about 5 mol % to 95 mol %, preferably from about 10 mol % to 90 mol %, of the total olefin-containing alkylation mixture. Propylene generally comprises from about 5 mol % to 95 mol %, preferably from about 10 mol % to 90 mol %, of such a mixture. The molar ratio of ethylene to propylene preferably ranges from about 90:1 to 1:90, more preferably from about 9:1 to 1:9.

As can be seen from the foregoing ranges, the total concentration of $C_2$ and $C_3$ olefins in the olefin-containing alkylation mixture need not be very high. In fact, the present process can be practiced with alkylating agents wherein the ethylene and propylene olefinic hydrocarbons are present in only minor quantities in gas streams. Thus, in contrast to many prior art processes, the normally gaseous olefinic alkylation mixtures for use in the process of the present invention need not be purified or concentrated. Normally gaseous olefinic hydrocarbons appear in minor concentrations in various refinery gas streams, usually diluted with various unreactive gases such as hydrogen, nitrogen, methane, ethane, propane, etc. These gas streams containing olefinic hydrocarbon are obtained in petroleum refineries from various refinery installations including thermal cracking units, catalytic cracking units, thermal reforming units, coking units, polymerization units, etc. Such refinery gas streams have in the past often been burned for fuel value since an economical process for their utilization as alkylating agents has not been available except where concentration of the olefinic hydrocarbons has been carried out concurrently therewith.

In addition to containing minor quantities of olefin hydrocarbons such as ethylene, propylene, and the various butenes, depending upon their source, refinery gas streams contain varying amounts of nitrogen, hydrogen, and various normally gaseous additional olefinic hydrocarbons. Thus, a refinery off-gas ethylene-propylene stream may contain hydrogen, nitrogen, methane, ethane and propane with the ethylene and propylene in minor proportions. A typical analysis in mol percent for a utilizable refinery off-gas from the catalytic cracking unit is as follows: nitrogen, 4.0%; carbon monoxide, 0.2%; hydrogen, 5.4%; methane, 37.8%; ethylene, 10.3%; ethane, 24.7%; propylene, 6.5%; propane, 10.7%; and $C_4$ hydrocarbons, 0.5%. It is readily observed that the total olefin content of this gas stream is 16.7%. Such gas streams containing olefinic hydrocarbons in minor or dilute quantities are preferred alkylating agents in accordance with the present invention.

In accordance with the process herein, such ethylene and propylene containing mixtures are used to selectively alkylate aromatic hydrocarbons. The catalyst employed to promote such selective alkylation is one which comprises a particular crystalline aluminosilicate zeolite material known as ZSM-12.

Zeolite ZSM-12 is a member of a particular class of zeolitic materials which exhibit unusual properties. Although such zeolites have unusually low alumina contents, i.e. high silica to alumina mole ratios, they are very active even when the silica to alumina mole ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by controlled burning at higher than usual temperatures to restore activity. These zeolites, used as catalysts, generally have low coke-forming activity and therefore are conductive to long times on stream between regenerations by controlled burning of carbonaceous deposits with oxygen-containing gas such as air.

An important characteristic of the crystal structure of this particular class of zeolites which includes ZSM-12 is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the ZSM-12 zeolite crystal and to exclude aluminum in the binder or in cationic or other form within the channels. Although zeolites with a silica to alumina mole ratio of at least 12 are useful, it is preferred in some instances to use ZSM-12 zeolites having substantially higher silica/alumina ratios, e.g. 90:1 and above. In addition, ZSM-12 type zeolites as otherwise characterized herein but which are substantially free of aluminum, that is ZSM-12 zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful ZSM-12 zeolites described herein, that is to say those ZSM-12 zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

Zeolites of the particular class useful herein including ZSM-12 have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10} (\text{fraction of hexane remaining})}{\log_{10} (\text{fraction of 3-methylpentane remaining})}$$

The Constraint Index approximates the ratio of the cracking rate constants for the two hydrocarbons. Zeolites suitable for the present invention are those ZSM-12 zeolites having a Constraint Index of about 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those ZSM-12 zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those ZSM-12 zeolites which, when tested under two or more sets of conditions within the above-specified ranges of temperature and conversion, produce a value of the Constraint Index slightly less than 1, e.g., 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

ZSM-12 is described in greater detail in U.S. Pat. No. 3,832,449 issued Aug. 27, 1974 to Rosinski and Rubin. The entire description contained within this patent, particularly the X-ray diffraction pattern of therein disclosed ZSM-12, is incorporated herein by reference.

In the ZSM-12 zeolite, the original cations can be subsequently replaced, at least in part, by calcination and/or ion exchange with another cation. Thus, the original cations can be exchanged into a hydrogen or hydrogen ion precursor form or a form in which the original cations have been replaced by a metal of, for example, Groups II through VIII of the Periodic Table. Thus, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing U.S. Pat. No. 3,832,449 to describe examples of specific members of the specified zeolite ZSM-12 class with greater particularity, it is intended that identification of the therein disclosed crystalline zeolite ZSM-12 be resolved on the basis of its respective X-ray diffraction patterns. As discussed above, the present invention contemplates utilization of such catalysts wherein the mole ratio of silica to alumina is essentially unbounded. The incorporation of the identified patent should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline ZSM-12 zeolite material. Furthermore, the ZSM-12 zeolites of the present invention preferably have a crystal size of from about 0.02 to 0.5 micron.

The specific zeolite ZSM-12, when prepared in the presence of organic cations, is substantially catalytically inactive, possibly because the intra-crystalline free space is occupied by organic cations from the forming solution. The zeolite may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

In a preferred aspect of this invention, the ZSM-12 zeolites herein are selected as those providing among other things a crystal framework density, in the dry hydrogen form, of not less than about 1.6 grams per cubic centimeter. It has been found that zeolites which satisfy all three of the discussed criteria are most desired for several reasons. Therefore, the preferred ZSM-12 zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in *PROCEEDINGS OF THE CONFERENCE ON MOLECULAR SIEVES*, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including others besides the ZSM-12 utilized in this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the ZSM-12 zeolite is conveniently converted to the hydrogen form, generally by intermediate formation of the ammonium form as a result of ammonium ion exchange and calcination of the ammonium form to yield the hydrogen form. In addition to the hydrogen form, other forms of the ZSM-12 zeolite wherein the original alkali metal has been reduced to less than about 1.5 percent by weight may be used in the process of the present invention. Thus, the original alkali metal of the ZSM-12 zeolite may be replaced by ion exchange with other suitable metal cations of Groups I through VIII of the Periodic Table, including, by way of example, nickel, copper, zinc, palladium, calcium or rare earth metals.

In practicing any given desired hydrocarbon conversion process including that of the present invention, it may be useful to incorporate the above-described crystalline ZSM-12 zeolites with a matrix comprising another material resistant to the temperature and other conditions employed in the process. Such matrix material is useful as a binder and imparts greater resistance to the catalyst for the temperature, pressure and reactant feed stream velocity conditions which may be encountered in the alkylation process.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the ZSM-12 zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

In accordance with the present invention, the ZSM-12 zeolite catalyst composition as hereinbefore described promotes surprisingly selective alkylation of aromatic hydrocarbons when such aromatic hydrocarbons are alkylated with an alkylation mixture containing both ethylene and propylene. Among the olefins present in such alkylation mixtures, propylene is selectively reacted with the aromatic hydrocarbons, thereby providing an aromatic mixture enriched in the propylated aromatic product, e.g., cumene, and a residual olefin-containing mixture enriched in the ethylene which does not react with the aromatic hydrocarbon. The ethylene-enriched mixture can thus be recovered from the alkylation reaction mixture and utilized in various petrochemical processes.

Such selective alkylation is accomplished by contacting the aromatic hydrocarbon reactant with the olefin-containing alkylation mixture in the presence of the ZSM-12 catalyst composition under alkylation conditions. Alkylation conditions include a temperature between about 100° C. and the critical temperature of the aromatic hydrocarbon reactant, preferably from about 150° C. to 300° C. The reaction generally takes place at atmospheric pressure, but the pressure may be within the approximate range of $10^5$ N/m$^2$ to $6 \times 10^6$ N/m$^2$ (1 atm to 60 atm). The molar ratio of aromatic hydrocarbon to the olefin in the alkylation mixture is preferably within the approximate range of 1:1 to 12:1. The reaction may be suitably accomplished utilizing a feed weight hourly space velocity (WHSV) of between about 0.5 and about 100, preferably between about 5 and about 40.

The process of this invention may be conducted with the organic reactants in either the gaseous or the liquid phase or both. It may be carried out as a batch-type, semi-continuous or continuous operation utilizing a fixed, fluidized or moving bed catalyst system.

The following examples will serve to illustrate the process of this invention but are not limiting thereof:

EXAMPLE I

PREPARATION OF ZSM-12

Zeolite ZSM-12 useful in the present invention can be prepared in the following manner: A solution of 96.2 grams tetraethylammoniumbromide and 17.5 grams NaOH and 300 grams $H_2O$ is made. Five grams of $NaAl_2$ (41.8% $Al_2O_3$) is dissolved in the solution. Five hundred grams of colloidal silica, e.g., Ludox, are added to the solution and mixed for 15 minutes. The resulting mixture is crystallized in a polypropylene jar without agitation for 84 days at 100° C. The product analysis by X-ray diffraction is ZSM-12 material with a $SiO_2/Al_2O_3$ ratio of 82. The product is washed and dried at 110° C. The dried powder is pre-calcined for 3 hours at 370° C. in air and then cooled to room temperature in a dessicator. This is followed by four contacts each with 10 ml. of 5% $NH_4Cl$/gram of calcined powder at 90° C. for 1 hour. Each contact is made with stirring. The product is washed free of $Cl^-$ ions at room temperature and then dried at 110° C. The sodium content of the zeolite at this stage is less than 0.01%. The dried powder is then calcined by heating it in air at 538° C. for 10 hours. The product is then cooled in a dessicator.

EXAMPLES II–IV

SELECTIVE BENZENE ALKYLATION

Alkylation of benzene is conducted in a glass reactor using a mixture of ethylene, propylene and inert gas as an alkylating agent and a hydrogen ZSM-12 zeolite of the same general type as that prepared in Example I as an alkylation catalyst. The HZSM-12 catalyst employed has a crystal size of about 0.05 micron. Four grams of such a catalyst composition were employed. Alkylation was carried out at atmospheric pressure and within the temperature range of from 210° C. to 250° C. using a $WHSV_b$ of 4.

The benzene reactant was admixed with both an "ethylene" stream and a "propylene" stream. The composition of the ethylene stream was 44.4 mol % of methane; 20.7% mol % ethane; 18.3 mol % ethylene; 16.5 mol % nitrogen and 0.11 mol % carbon dioxide. The propylene stream contained a 1:1 weight ratio of propane and propylene.

Temperature conditions, flow rates and feed component ratios, as well as conversion and selectivity results for benzene alkylation, are set forth in Table I.

TABLE I

ALKYLATION OF BENZENE WITH DILUTE ETHYLENE-PROPYLENE STREAM

| Example No. | II | III | IV |
|---|---|---|---|
| Catalyst | | HZSM-12 | |
| | | (4.0 gms) | |
| Temperature (°C.) | 210 | 225 | 250 |
| Pressure | | Atmo. | |
| Flow Rate | | | |
| Benzene (cc/hr) | | 20.0 | |
| Ethylene Stream (cc/min) | | 56.0 | |
| Propylene Stream (cc/min) | | 27.4 | |
| Molar Feed Ratio Benzene/Ethylene/Propylene | | 6.6/0.75/1.00 | |
| % Conversion Propylene | 100 | 100 | 99 |
| % Conversion Ethylene | | Very Low | |
| % Propylene Conv. to Propylbenzenes Selectivity | 98 | 100 | 100 |
| Cumene/Cumene & Diisopropylbenzene(mole) | 90 | 90 | 94 |
| Cumene/Cumene & Ethylbenzene(mole) | 99 | 99 | 98 |
| % Para in Diisopropylbenzene(mole) | 31 | 29 | 27 |

The Table I data indicate that the ZSM-12 zeolite catalyst promotes highly selective propylation of benzene with very low conversion of ethylene when dilute olefin streams containing a mixture of ethylene and propylene are used as the alkylating agent. Propylene, in fact, is reacted completely out of the olefin stream leaving a gas stream enriched in ethylene and free of reactive propylene.

EXAMPLES V–VII

Benzene alkylation using an alkylating agent containing only an ethylene/propylene mixture is conducted in the same general manner as employed in EXAMPLES II–IV described above. In such testing a $WHSV_b$ of 8 is employed. Temperature conditions, flow rates and conversion/selectively results are shown in TABLE II.

TABLE II

ALKYLATION OF BENZENE WITH CONCENTRATED ETHYLENE-PROPYLENE STREAM

| Example No. | V | VI | VII |
|---|---|---|---|
| Catalyst | | HZSM-12 | |
| | | (4.0 gms) | |
| Temperature (°C.) | 200 | 225 | 250 |
| Pressure | | Atmo. | |
| Flow Rate | | | |
| Benzene (cc/hr) | | 40.0 | |
| Ethylene Stream (cc/min) | | 18.2 | |
| Propylene Stream (cc/min) | | 18.8 | |
| % Conversion Propylene | 99 | 100 | 100 |
| % Conversion Ethylene | 31 | 34 | 40 |
| % Propylene Conv. to Propylbenzenes Selectivity | 69 | 59 | 64 |
| Cumene/Cumene & Diisopropylbenzene(mole) | 98 | 97 | 94 |
| Cumene/Cumene & Ethylbenzene(mole) | 92 | 95 | 97 |

The TABLE II data demonstrate that, even with more concentrated ethylene/propylene mixture, benzene alkylation is still highly selective to the cumene product with very little diisopropylbenzene produced.

What is claimed is:

1. A process for selectively alkylating benzene with an olefin-containing alkylation mixture comprising ethylene and propylene, said process comprising contacting benzene with an alkylation mixture comprising from about 5 to 95 mole % ethylene, and from about 5 to 95 mole % propylene, in the presence of a ZSM-12 based alkylation catalyst composition under alkylation conditions, to thereby produce an alkylbenzene product enriched in propylated benzene to the extent of at least 98% selectivity based on moles of propylated benzene per mole of propylated benzene plus ethylated benzene, and an olefin-containing product enriched in ethylene and free of reactive propylene.

2. A process according to claim 1 wherein said alkylation conditions include a temperature of from about 150° to 300° C., a pressure of from about $10^5$ to $6 \times 10^6$ N/m² and a feed weight hourly space velocity of between about 0.5 and about 100.

3. A process according to claim 2 wherein the molar ratio of benzene to the total olefin in the alkylation mixture is within the range of from about 12:1 to 1:1.

4. A process according to claim 3 wherein the alkylation mixture comprises from about 10 mol % to 90 mol % ethylene and from about 10 mol % to 90 mol % propylene.

5. A process according to claim 4 wherein the zeolite in said ZSM-12-based alkylation catalyst composition has a silica/alumina mole ratio of at least about 90:1 and a crystal size of from about 0.02 to 0.5 micron.

6. A process according to claim 5 wherein said zeolite ZSM-12 is combined with a binder therefor to form said catalyst composition.

* * * * *